(12) United States Patent
Chock et al.

(10) Patent No.: US 7,377,643 B1
(45) Date of Patent: May 27, 2008

(54) METHOD AND APPARATUS FOR EYE IMAGING WITH POSITION REGISTRATION AND CONSTANT PUPIL SIZE

(75) Inventors: Ernest P. Chock, Santa Monica, CA (US); Dale E. Winther, La Crescenta, CA (US)

(73) Assignee: Q Step Technologies, Inc., Pasadena, CA (US)

( * ) Notice: Subject to any disclaimer, the term of this patent is extended or adjusted under 35 U.S.C. 154(b) by 441 days.

(21) Appl. No.: 10/710,955

(22) Filed: Aug. 13, 2004

(51) Int. Cl.
*A61B 3/14* (2006.01)

(52) U.S. Cl. ........................................ 351/208; 351/205
(58) Field of Classification Search ........ 351/205–223, 351/246
See application file for complete search history.

(56) References Cited

U.S. PATENT DOCUMENTS

| | | | |
|---|---|---|---|
| 5,433,197 A | 7/1995 | Stark | 600/319 |
| 6,827,444 B2 * | 12/2004 | Williams et al. | 351/212 |
| 6,948,818 B2 * | 9/2005 | Williams et al. | 351/211 |
| 2004/0218241 A1 * | 11/2004 | Roh | 359/35 |

* cited by examiner

*Primary Examiner*—M. Hasan
(74) *Attorney, Agent, or Firm*—George G. C. Tseng; McDermott Will & Emery LLP (57) ABSTRACT

A method for capturing an image of an eye having an iris, including the steps of determining a plurality of measurement origins in the image; detecting an edge of the iris; determining a distance from each measurement origin to the edge of the iris; and, outputting a final image when each of the determined distances is equal to respective one of a plurality of predetermined lengths. A computer-readable medium containing computer-executable instructions for causing a computer to perform the above-described method is also described. An apparatus having an image sensor and a processor for performing the method is also described.

21 Claims, 8 Drawing Sheets

METHOD AND APPARATUS FOR EYE IMAGING WITH POSITION REGISTRATION AND CONSTANT PUPIL SIZE

BACKGROUND OF INVENTION

The present invention relates generally to capturing images of an eye, and more particularly, to a method and apparatus for eye imaging with position registration and constant pupil size.

In the U.S., approximately 17 million people have diabetes; worldwide there are about 170 million. According to a recent estimate, at the current rate of increase, due to genetic makeup and economic growth, it is expected that the worldwide total population of diabetics may reach half a billion by 2008.

An important aspect of the management of diabetes is the constant monitoring of the blood serum glucose level. Current glucose measurement techniques involves pricking the finger with a lancet, and wicking the blood onto an electrochemical test strip that provides the electrical data read by a glucose meter. Many patients attempt to avoid these painful and uncomfortable tests, to the detriment of their health. The problem is especially acute among children.

To address the problem raised by invasive glucose measurement techniques, several non-invasive diagnostic methods have been proposed. One non-invasive diagnostic method for measuring glucose and other analytes of biomedical interest in humans is measuring changes in images of the eyes. This technique is based in part on the fact that some features of the eye have long term stability and that each individual has a unique iris pattern. Also, as the eye is self-cleaning, therefore minimizing contaminants that could interfere with the measurements, it provides an ideal site for diagnostic measurements.

In this method, images of the eye are captured and processed with a complex and sophisticated algorithm to determine a corresponding glucose level in the blood serum. However, in order to make consistent comparisons of the image data, it is necessary to hold constant some of the variables, such as the radiation wavelength and intensity, radiation pulse duration, orientation of the eye, and area coverage of the eye. Although the radiation and other characteristics may be easily reproduced, as they are provided by electronic devices and circuits, it is difficult to manipulate the eye orientation with respect to the measuring instrument, area coverage, and iris area of the eye to achieve consistent results using eye imaging techniques.

Accordingly, there is a need to overcome the issues noted above to achieve imaging of the eye with consistent parameters.

SUMMARY OF INVENTION

In one embodiment, the present invention is a method for capturing an image of an eye having an iris, including the steps of determining a plurality of measurement origins in the image; detecting an edge of the iris; determining a distance from each measurement origin to the edge of the iris; and, outputting a final image when each of the determined distances is equal to respective one of a plurality of predetermined lengths.

In another embodiment, the present invention is a method for capturing an image of an eye, the eye having an iris and a pupil. The method includes the steps of determining a size and location of one of the iris and the pupil; comparing the determined size and location to a predetermined size and position; and, outputting a final image if the size and location matches the predetermined size and position, respectively.

In yet another embodiment, the present invention is a method for capturing an image of an eye, the eye including a pupil with a size. The method including the steps of manipulating the size of the pupil by exposing the pupil to a light starting at a first intensity level and ending at a second intensity level; determining the size of the pupil; and, outputting a final image when the size of the pupil matches a predetermined size.

In still yet another embodiment, the present invention is a method for auto-positioning and auto-triggering of a capture of an eye image. The method including the steps of capturing a first image of an eye having a pupil, the first image having four corners; detecting an edge of the pupil; and, determining a distance from each corner of the image to the edge of the pupil along two diagonal paths, each diagonal path defined by two diagonally opposing corners of the first image.

In other embodiments, the present invention is implemented as a computer-readable medium containing computer-executable instructions that causes a computer to perform the inventive methods.

In yet other embodiments, the present invention is implemented as an apparatus including an image sensor and a processor for performing the method.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF DRAWINGS

The invention may be more readily understood by referring to the accompanying drawings in which.

Like numerals refer to like parts throughout the several views of the drawings.

DETAILED DESCRIPTION

The present invention addresses issues related to conditioning an eye for image capture so that the captured images have consistent parameters. The present invention includes an imaging system controlled by an algorithm for positioning and registration of the eye for image capture. The algorithm provides for both (a) the positioning of the iris and pupil image in the image capturing system, and (b) the scaling of the size of image of the pupil (i.e., the inner diameter of the iris) to a preset diameter before capturing the image. The present invention provides various means of acquiring eye image data with consistent reference parameters such as the diameter of the pupil, diameter of the iris, eye orientation with respect to the image, image coverage, and position of distinctive marks in the iris. Comparative analysis of such image data, with the specified constant parameters allows for the determination of biological analytes such as glucose concentration. These parameters can be used to provide base-line references to be held constant for calibration or comparison of image data for analysis. The advantages of the present invention include the ease of registering the position and size of the pupil and iris for the purpose of establishing a calibration curve of analyte concentration as a function of image characteristics.

Generally, certain parameters are held constant for comparative analyses of the eye images. This process of acquiring the specified parameters such as position (e.g. centering), pupil size, iris size, and orientation with respect to the image capturing instrument, are achieved by one or more of the following approaches:

1. Measurement of the pupil size and location through tracking of the diagonal distances from the corners to the image to edge of the pupil;

2. Measurement of the iris diameter and location through tracking of the diagonal distances from the edge of the iris (the limbus) to the corner of the image; and 3. Measurement of the correlation of the reflection of light from the surfaces of the lens, from the epithelial and endothelial surfaces of the cornea, and from the retina. These are the Purkinje images well known to practitioners of the art of optical eye tracking.

This invention involves the methods for capturing eye images for the purpose of biomedical image analysis to determine the content or concentration of analytes such as glucose. The approach involves keeping constant the positioning, the registration and orientation of the eye for automatic computer image capture. Such constant conditions allow for establishment of a calibration curve and subsequent analysis of the analytes. The method includes one or more of the following: pre-set distances to the edge of the pupil and/or the iris; correlation of reflections from the surfaces of the cornea and lens; registration of reference feature marks on the iris, manipulation of the pupil size through lighting, and audio or text guiding of manual eye movement and manual or automatic instrument adjustment.

Figure 1:
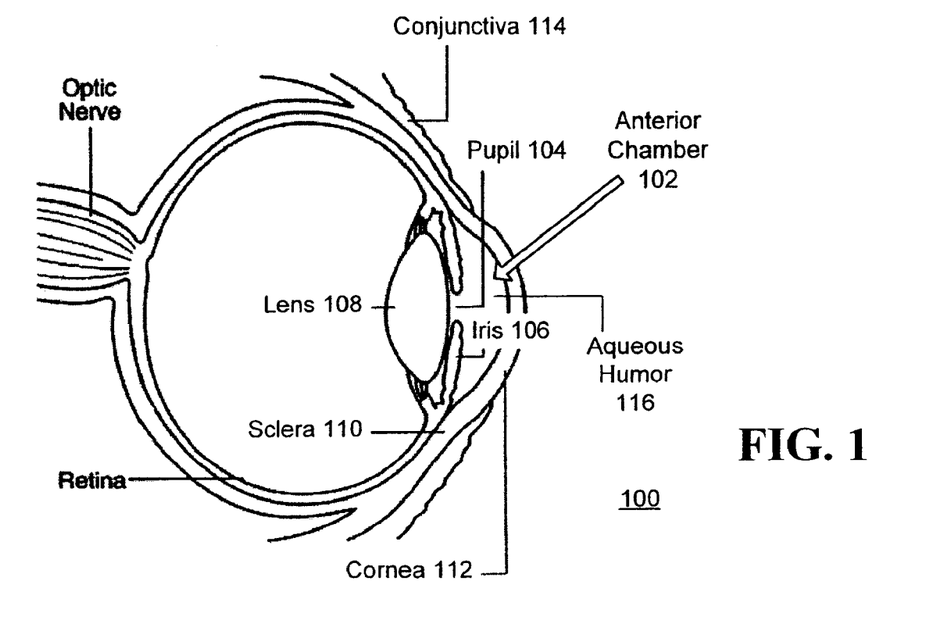
FIG. 1 is an illustration of an eye used to describe a method and apparatus for eye imaging with position registration and constant pupil size configured in accordance to one embodiment of the present invention.

FIG. 1 is an illustration of an eye 100 of a subject used in the description of the various embodiments of the present invention. Eye 100 includes an anterior chamber 102 defined by a lens 108 and a cornea 112 that is filled with the aqueous humor (a gel-like substance) 116, and an iris 106, the colored part of the eye. The glucose level contained in the blood serum is tracked closely by one or more of the components in the anterior chamber of the eye, i.e., the cornea 112, aqueous humor 116, and/or the iris 106. Eye 100 also includes a pupil 104 (the lens, or, the "dark" center of the eye) ringed by an iris 106, which is itself surrounded by a sclera 110 (the "whites" of the eye). A conjunctiva 114 covers the upper and lower portions of sclera 110.

Figure 2:
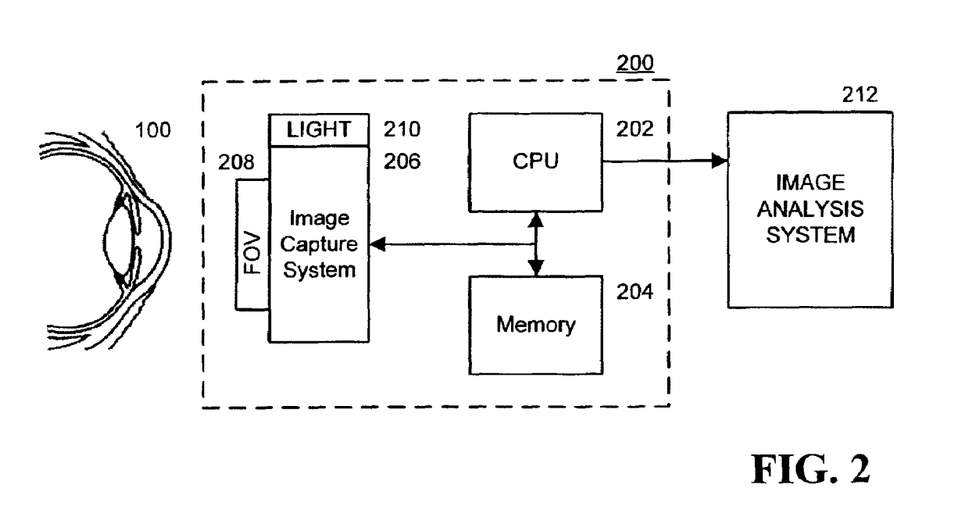
FIG. 2 is a block diagram of an eye imaging system configured in accordance with one embodiment of the present invention.

FIG. 2 is a block diagram of an eye imaging system 200 configured in accordance with one embodiment of the present invention, coupled to an image analysis system 212. Eye imaging system 200 includes a central processing unit (CPU) 202, a memory 204, and an image capture system 206. Image capture system 206 includes a field of view (FOV) device (camera) 208 that defines the parameter of the field of view of image capture system 206. In one embodiment, FOV 208 includes a lens system that has a predetermined focal length. In another embodiment, camera 208 may include a lens system that has characteristics changeable based on the desired parameters of the image to be captured. For example, the lens system of camera 208 may provide zooming capability to increase or decrease the field of view parameters.

Image capture system 206 includes an image sensor such as a charge-coupled device (CCD) image sensor or any digital image sensor. The specific implementation of the image sensor in image capture system 206 is known by one of ordinary skill in the art. Image capture system 206 also includes a light source 210 by which appropriate illumination is provided to eye 100 to both illuminate eye 100, and manipulate the dilation of pupil 104, as further described below. Light source 210 may be implemented as one or more light generating devices such as light bulbs, light emitting diodes (LED), or low power lasers. Thus, several LED's may be used in light source 210. In another embodiment, the illumination is provided by a display such as that used for displaying computer images.

In still yet another embodiment, light source 210 may be composed of light sources of different operating characteristics, such as LED's, or low power lasers, with different emission wavelengths, or even a mix of the described devices.

In one embodiment, CPU 202 may be an application specific integrated circuit (ASIC) configured specifically to implement features of eye imaging system 200. In another embodiment, CPU 202 may be a general purpose processor such as those produced by Advanced Micro Devices (AMD), Inc. or Intel Corp. In yet another embodiment, the processing performed by CPU 202 may be accomplished by a separate computer system. Memory 204, may be integrated in CPU 202 or it may be a non-integrated memory component. Memory 204 is used for storing program code for managing the operation of eye imaging system 200, captured images, and data related to the captured images. Further, the function provided by memory 204 may be provided by any of the memory devices available for computer systems.

Figure 3:
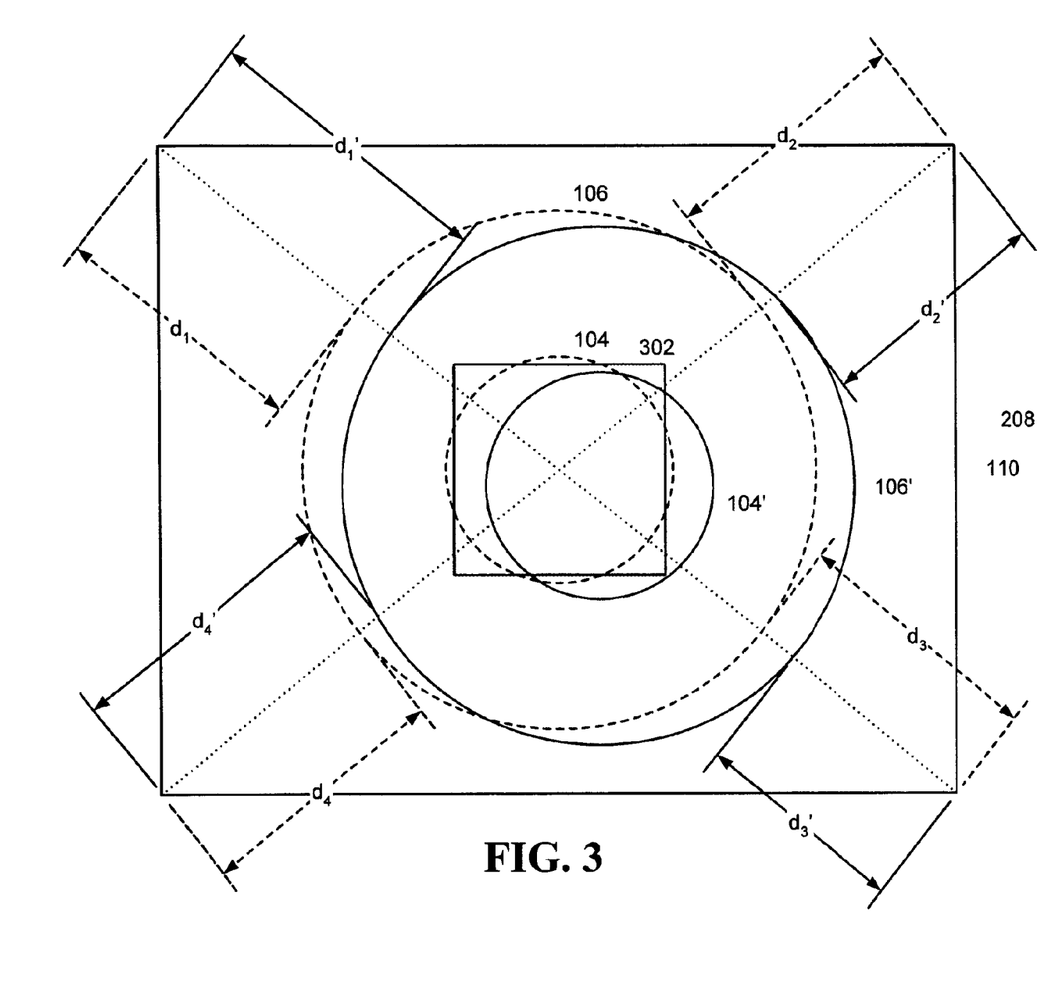
FIG. 3 is an illustration of an eye image captured through a field of view of an image capture system of the eye imaging system of FIG. 2 configured in accordance with one embodiment of the present invention.

In one embodiment of the present invention, real-time images of anterior chamber 102 of eye 100, including sclera 110, aqueous humor 116, pupil 106 and iris 106, are input into eye imaging system 200 and processed by an algorithm that calculates the distance from each corner of FOV 208 to the edge of the iris 106-sclera 110 boundary (sclera spur), along a pair of diagonal lines shown as d1', d2', d3' and d4' in FIG. 3. Eye imaging system 200 will trigger an image capture and output a final image when, through manipulation of the position of eye 100 and/or the imaging system 200, distances d1', d2', d3' and d4' match preset values within prescribed tolerance. If the desired position of the iris image is to be at the center of the image, the preset values would be d1=d2=d3=d4 with a preset tolerance of +/−3%, for example. The required position can be arrived at by movement of the eye, adjustment of the distance between the eye and the apparatus, and/or adjustment of the optical system, depending on the optical system employed. The criteria for determining the length of distances d1', d2', d3' and d4' along the diagonals is based on length measurement and edge detection techniques well known to practitioners of computer imaging.

Figure 7:
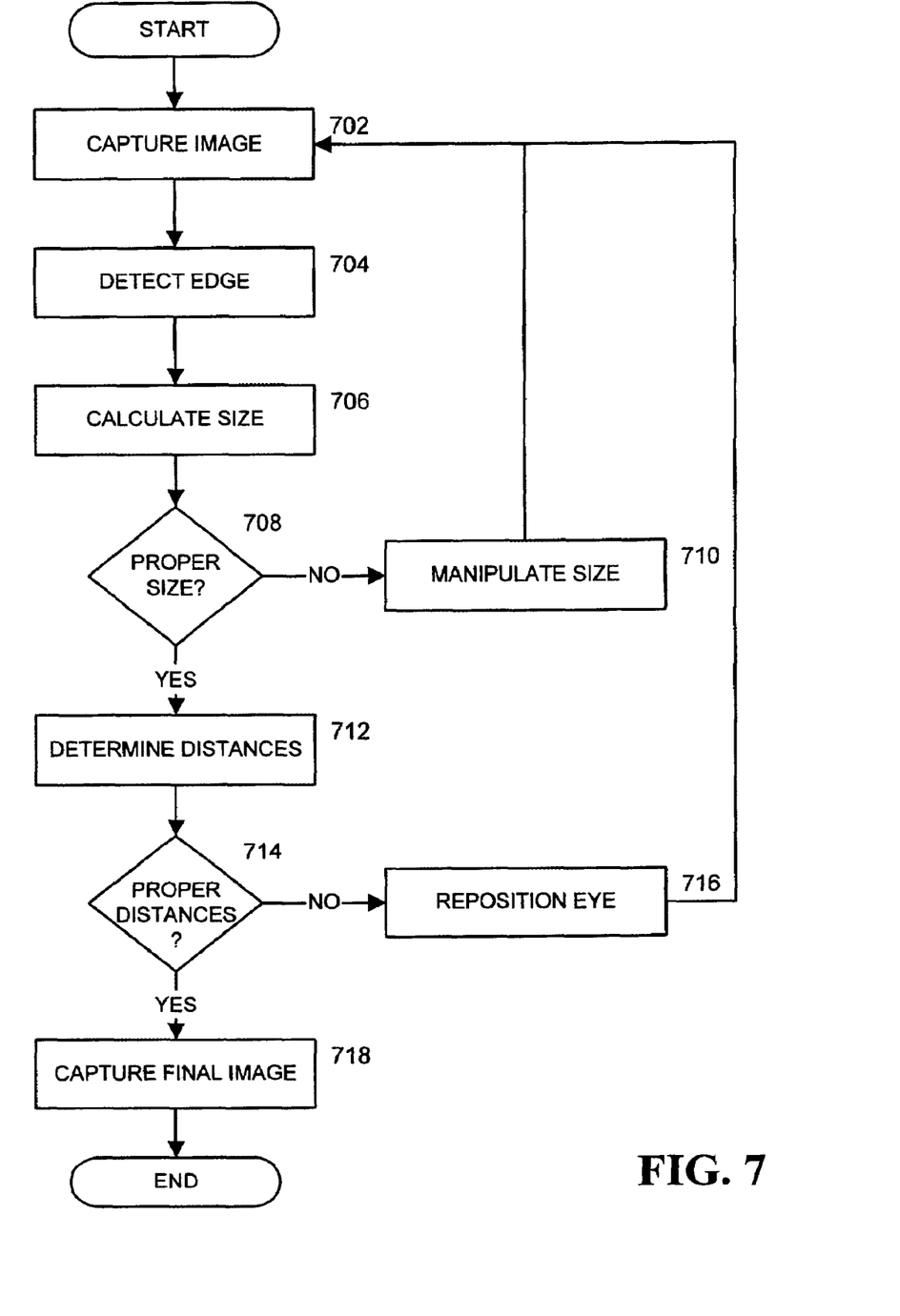
FIG. 7 is a flow diagram of the operation of the eye imaging system of FIG. 2 in accordance with one embodiment of the present invention.

With reference to the flow diagram in FIG. 7, in step 702, eye imaging system 200 captures an image of eye 100 with image capture system 206. As discussed above, the image is taken with a size limited to the imaging plane size of camera 208. In the exemplary application of eye imaging system 200 in the diagnostic system, only the image data related to iris 106 and pupil 104 is of interest. Thus, it is desirable to restrict the image data obtained to exclude as much of sclera 110 as practical. In one embodiment, the field of view of image capture system 206, as bounded by FOV 208, is set to be only as large as necessary to encompass the outer edge of iris 106. In this embodiment, FOV 208 contains a lens system which may include a zoom lens, for example. The eye imaging system 200 will operate the lens system to zoom in the field of view to capture as little image data of sclera 110 as possible, thereby maximizing the amount of image data acquired of iris 106 and pupil 104. First, eye imaging system 200 will locate the edge of iris 106 using an edge detection algorithm contained in memory 204, as discussed further below. Eye imaging system 200 will continuously search for an image that matches the prescribed parameters of d1, d2, d3 and d4. Variation of the parameters can be accomplished by movement of the eye position, and/or by shining light radiation on the eye to shrink or enlarge the pupil size.

Once an image matches the prescribed requirements prescribed d1, d2, d3 and d4—the data for the image is captured and stored in the computer memory for further image analysis.

In another embodiment, the image-triggering threshold can be set as the distances from the edge of the iris to prescribed edges of the FOV. An exemplary image with FOV 208 is shown in FIG. 3.

In one embodiment, the darkest pixels within a center portion of the eye image are initially identified as pixels related to pupil 104. An average intensity is calculated for the dark area, within a 25×25 pixels region, for example, and established as the average intensity (grey level) of the pupil area for comparison against the surrounding iris area. Areas with light intensity below such average value of the dark area are then regarded as "non-pupil," or iris, for example. Similarly, a dividing line can be established along the limbus, between the iris and the sclera. A tolerance level of say, 5 counts in a 0 to 250 intensity levels, may be added to ease the triggering threshold if necessary. Different set of intensities or grey levels may also be established for different wavelength. The intensity level is used to determine the pixels belonging to iris 106, or sclera 110. The lightest pixels on the corner portions of the image are initially identified as pixels related to sclera 110. The distances d1, d2, d3 and d4 are the parameters prescribed for triggering the image capture.

Figure 4:
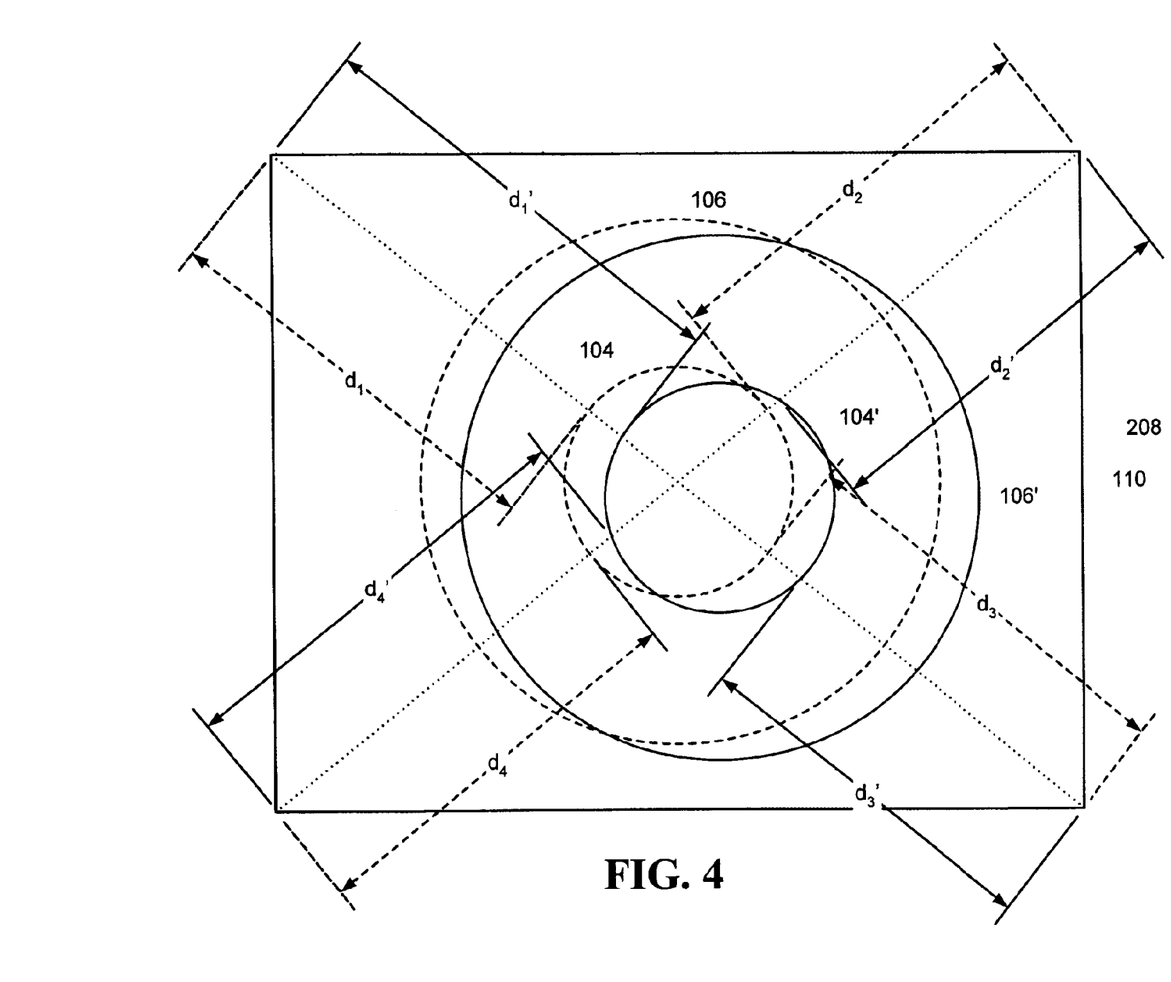
FIG. 4 is an illustration of an eye image captured through a field of view of an image capture system of the eye imaging system of FIG. 2 configured in accordance with another embodiment of the present invention.
Figure 5:
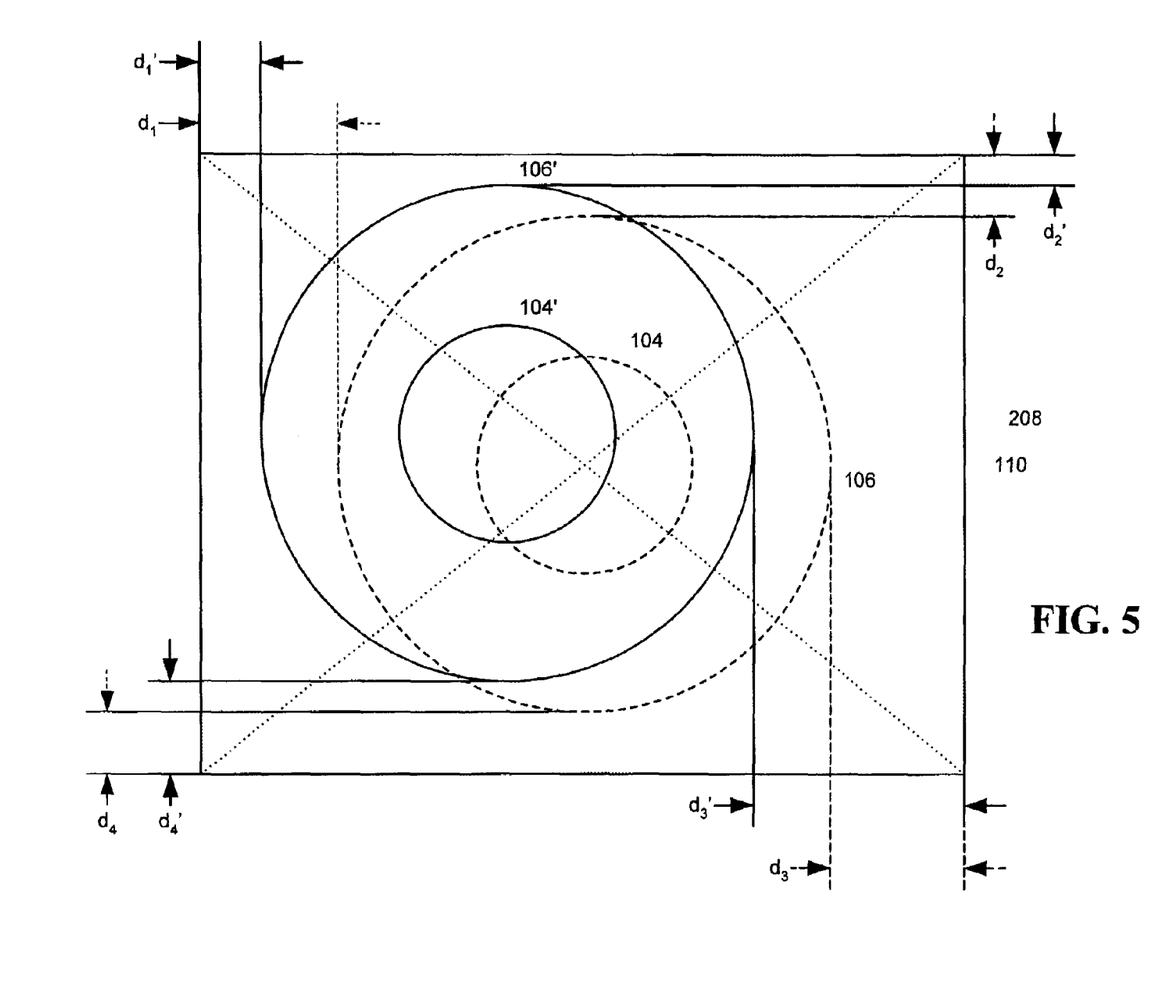
FIG. 5 is an illustration of an eye image captured through a field of view of an image capture system of the eye imaging system of FIG. 2 configured in accordance with yet another embodiment of the present invention.

In one embodiment, as illustrated in FIG. 3, distances d1, d2, d3 and d4 refer to the distances from the corner of the FOV image to the outer edge of the iris 106. In another embodiment, as illustrated in FIG. 4, distance d1, d2, d3 and d4 refer to the distances from the corner of the FOV image to the inner edge of the iris 106. In yet another embodiment, as illustrated in FIG. 5, distances d1, d2, d3 and d4 refer to the distances from the edges of the FOV of the image to the outer edge of the iris 106.

Figure 6:
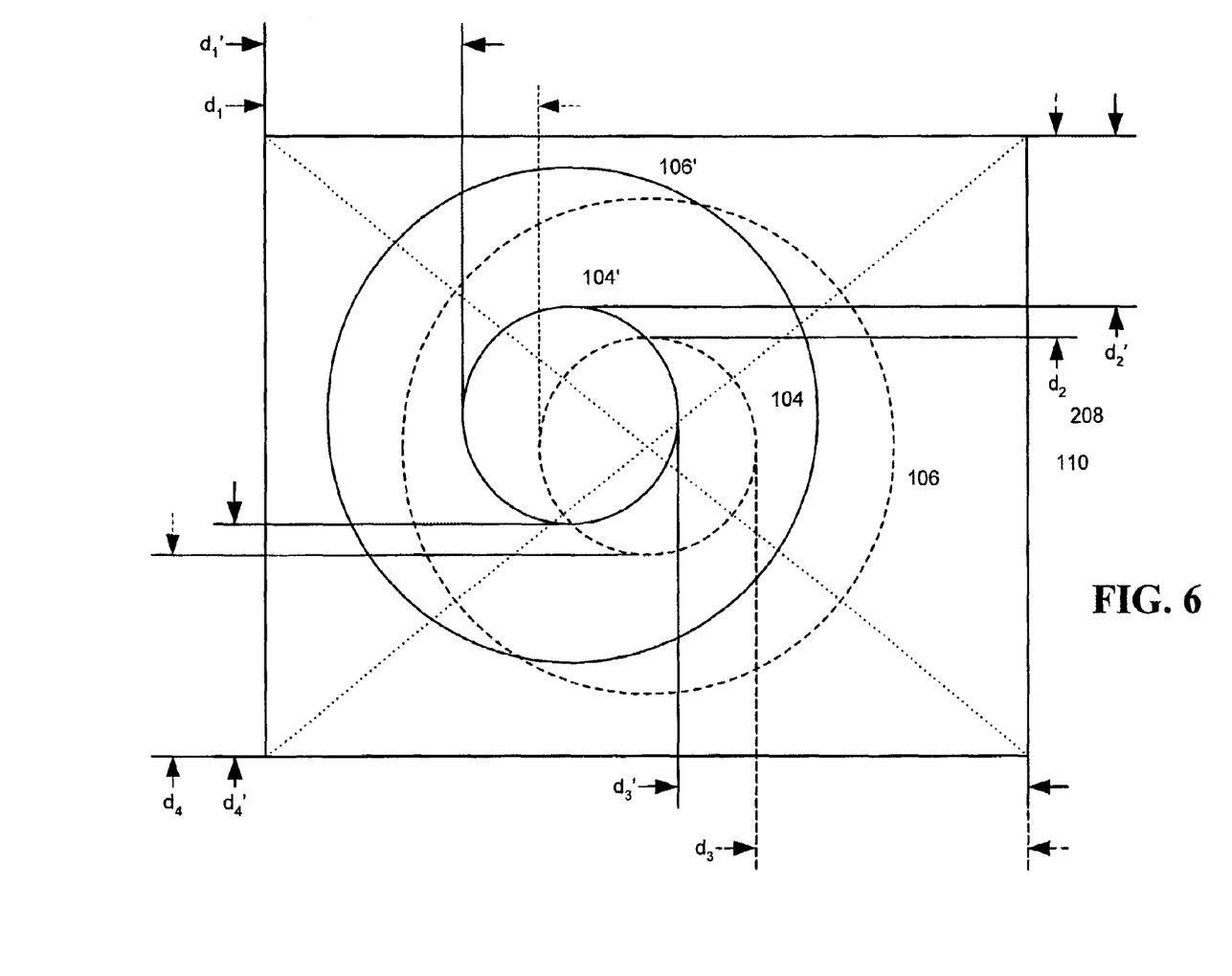
FIG. 6 is an illustration of an eye image captured through a field of view of an image capture system of the eye imaging system of FIG. 2 configured in accordance with still yet another embodiment of the present invention.

In still yet another embodiment, as shown in FIG. 6, d1, d2, d3 and d4 refer to the distances between the edges of the FOV of the image and the circumference of the pupil. In yet another embodiment, a specific feature in iris 106 is selected as a reference point to identify a specific orientation for an individual. A specific dark spot or feature on the iris at a certain position or dimension with respect to the FOV, for example, may be used as a reference point to determine orientation and/or registration for the specific individual.

Figure 8:
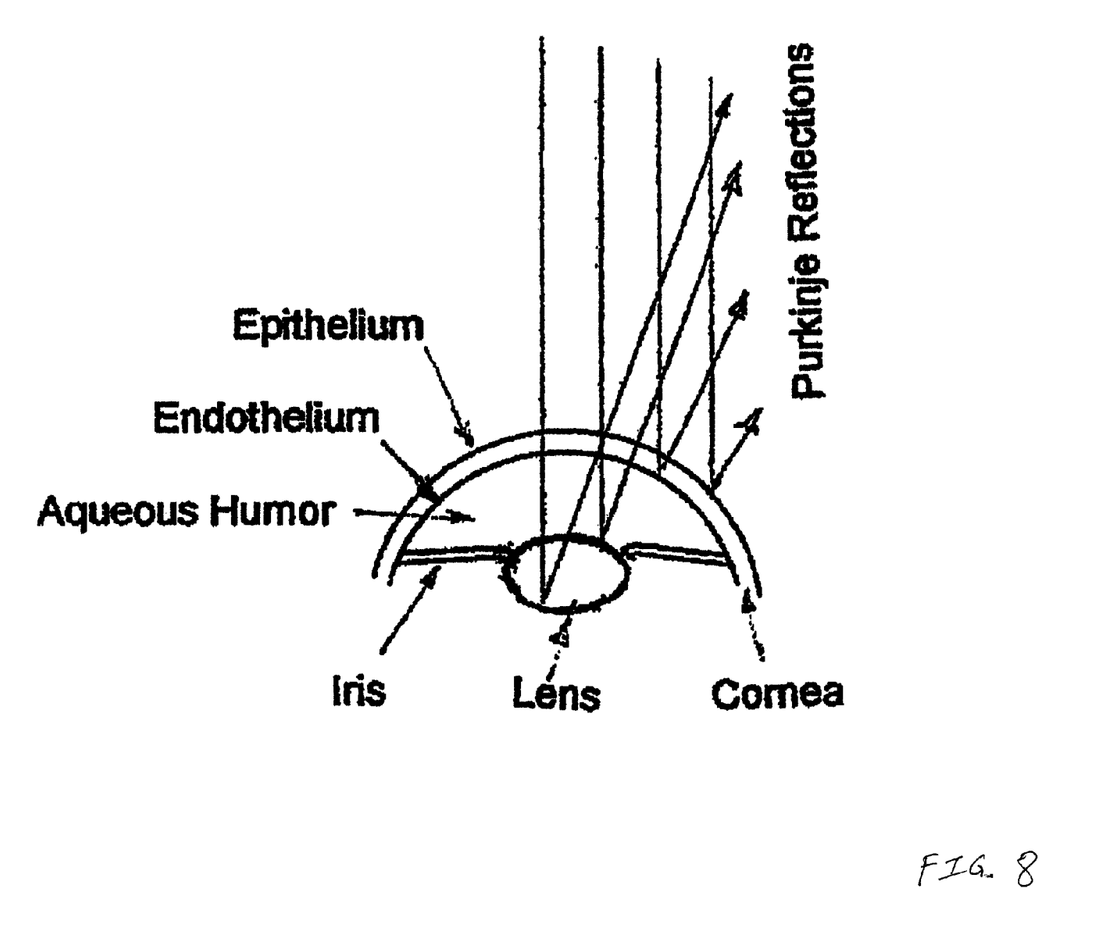
FIG. 8 illustrates the light reflections of the surfaces of the cornea and the lens. Such reflections are used to calculate and correlate the orientation of the eye.

FIG. 8 illustrates the light reflection from the surfaces of the cornea and the lens which are to be collected for calculation with computer algorithm to determine and track the orientation and registration of the eye.

In addition to the edge detection techniques described above, other edge detection techniques may be employed. Once the edges of interest have been detected, operation then continues with step 706.

In step 706, the size of selected parts of eye 100 are calculated. In one embodiment, once the parameters of FOV 208 of eye imaging device 200 are known, the size of a selected area in the image, the pupil for example, may be determined, based on the number of pixels included in the area that meet the gray-level defined for the pupil 104. Such techniques are known to one of ordinary skill in the art. Similarly, the area of the iris may also be determined. Edge-detection technique may also be used to determine the location or extent of the iris for orientation calculation, e.g. for finding the center. A tolerance parameter is often required for practical reasons, since the eye tends to move.

In step 708, CPU 202 detects whether the determined parameter in step 706 matches a predetermined size parameter within tolerance for the respective size. For example, if the size of pupil 104 is the size of interest that is determined in step 706, then it is compared to a predetermined parameter for pupil 104. Preferably, the predetermined parameter is a size of pupil 104 that was previously captured as a reference image for the particular person. If the size of iris 106 meets the criterion set in the reference image for the subject, an image capture is triggered. In another embodiment, a ratio between pupil size and iris size may be pre-set and image capturing system 200 triggers an image capture when the ratio met. If the prescribed parameter or ratio is not met, then operation will continue with step 710. As described below, the system repeatedly tests the parameter and ratio while the optical setting, the apparatus position and orientation are varied until the computer determines that the prescribed parameter or ratio is met.

In step 710, where the determined size is not the proper size, CPU 202 will alter the operating characteristics of image capture system 206, camera 208 and light source 210 to manipulate the determined size. CPU 202 automatically adjust the optical system by varying the intensity of light source 210, for example, to manipulate the pupil size, and/or adjusting the zoom lens to acquire the desired iris or pupil size before triggering image capture system 206. For example, the diameter of pupil 104 (inner diameter of iris 106) is manipulated to expand or shrink to reach the predetermined size through the use of light source 210 outputting light in the visible range. In one embodiment, only eye 100 is illuminated and swept through a range of brightness to drive the size of pupil 104 to change to the predetermined value. In another embodiment, both eyes could be driven simultaneously. In yet another embodiment, based on the principle that when one eye is exposed to bright light to shrink its pupil size the other pupil also shrinks in synchrony, the pupil size of the eye being examined may be manipulated by exposing the other eye to light of varying intensity. Thus, the pupil size 104 of the eye under examination may be manipulated by varying the light intensity of the other eye. Capture is then triggered when the desired size is matched.

The manipulation of the size of pupil 104, regardless of which eye is used as the exposed eye (or whether both eyes are used), can be accomplished using one of the following methods. In one embodiment, the manipulation is accomplished by flashing a bright pulse of light, which causes the pupil to contract, and then allowing the pupil to slowly expand after the pulsed light is turned off. In another embodiment, the size of pupil 104 can be manipulated by slowly ramping up or down the brightness of light source 210 until pupil 104 reaches the desired pre-determined size.

To manipulate the diameter of iris 106, the lens system of FOV 208 may zoom in or out so that iris 106 may be larger or smaller, as described above in step 702. In another embodiment, eye 100 may be moved closer or farther away from FOV 208. In yet another embodiment, the captured image may be scaled through software algorithms so that iris 106 is of a proper size.

In step 712, after it has been determined in step 708 that the proper size has been achieved, CPU 202 will determine if eye 100 is in the proper position by measuring the distances from a set of measurement origins to a feature of eye 100. In one embodiment, the measurement origins are the corners of FOV 208 and CPU 202 determines distances d1', d2', d3' and d4' from the corners of FOV 208 to iris 106, as shown in FIG. 3. Specifically, the distances are measured by determining the lengths from each of the four corners of FOV 208 to the edge of iris 106. In other embodiments, distances d1', d2', d3' and d4' may be measured from each corner of FOV 208 to the edge of pupil 104 along the diagonal lines, as shown in FIG. 4; from each side of FOV 208 to the edge of iris 106, as shown in FIG. 5; or from each side of FOV 208 to the edge of pupil 104 along diagonal lines, as shown in FIG. 6.

In step 714, CPU 202 compares distances d1', d2', d3' and d4' to detect whether these distances are either equal in length or within a particular tolerance of being equal. If it is determined that distances d1', d2', d3' and d4' are identical in length, as shown by distances d1, d2, d3 and d4, then eye 100 is in the proper position and operation will continue with step 718. Otherwise, operation continues with step 716. In another embodiment, instead of comparing distances d1', d2', d3' and d4' to each other, CPU 202 will compare distances d1', d2', d3' and d4' to the lengths of a set of predetermined distances. In this embodiment, distances d1', d2', d3' and d4' do not have to be equal, but instead may be predetermined using a previously captured image having a set of distances with lengths that are not equal. For example, if it is desirable to compare all images captured by eye imaging system 200 to a reference image that has prescribed distances d1, d2, d3 and d4 that are not equal, then these distances should be used.

In step 716, where it has been determined that iris 106 and pupil 104 are not in the proper position, either eye imaging system 200 can initiate the repositioning of iris 106 and pupil 104 with respect to FOV 208, or, the operation may be achieved manually. In one embodiment, the system generates an audio warning, such as tone or an audio and/or visual warning message when iris 106 and pupil 104 are far from specification. In another embodiment, eye imaging system 200 displays the image captured in step 702 so that is viewable by the subject and superimposes an eye feature (e.g., pupil or iris) position marker in the center of the image so that the subject can move eye 100—and consequently iris 106 and pupil 104 to the proper position. The use of the eye feature position marker provides the subject with a visual feedback as to how closely iris 106 and pupil 104 are centered. For example, FIG. 3 includes a square 302 as a pupil position marker. Other geometric shapes or graphic elements, including but not limited to such as elements as circles, triangles, octagons, rectangles, lines, or brackets, may be used. In yet another embodiment, eye imaging system 200 prompts the subject to move iris 106 and pupil 104 by displaying or vocalizing a text message to the subject. In still yet another embodiment, eye imaging system 200 will simply return to step 702 and capture another image, with the assumption that the subject will move iris 106 and pupil 104. In yet further another embodiment, eye imaging system 200 may also include a mechanism for physically moving the lens system in FOV 208 to center iris 106 and pupil 104. Preferably, image exposure may be of the order of milliseconds which therefore allowing for easy re-capture if necessary.

In step 718, upon CPU 202 detecting that the determined distances satisfy the preset criteria, thereby determining that the lengths of distances d1', d2', d3' and d4' are at the desired lengths. CPU 202 will send a command to output an image, referred to as a "final" image, to image analysis system 212. In one embodiment, where a single image is being taken, CPU 202 can output the latest image captured, which is the image used to determine that all the parameters are acceptable in step 714, to image analysis system 212. In another embodiment, eye imaging system 200 will capture a new image to be output as the final image. The final image may have a different set of parameters from the image used in the previous steps. For example, the final image may have a different resolution, size, or field of view from the image captured in step 702. Thus, the image captured in step 702 may have a field of view that is larger than iris 106, but when the final image is captured in step 718, CPU 202 will determine the edge of iris 106 and adjust FOV 208 to zoom in to iris 106 and allow iris 106 to fill up the field of view as much as possible. Similarly, if the image captured in step 702 has a field of view that is smaller than iris 106, but all other parameters are determined to be acceptable by CPU 202, then CPU 202 will adjust FOV 208 to zoom out such that the field of view encompasses iris 106 completely.

In another embodiment, CPU 202 may capture the final image in step 718 with light source 210 outputting light with different wavelengths. For example, light source 210 may output light with wavelengths in the infrared range as well as the visible range. Alternatively, light source 210 may output light with wavelengths centered around particular wavelengths, such as 470 nanometers (nm) (blue), 525 nm (green), 625 nm (red), 780 nm (amber), or 940 nm (near infrared). Further, light source 210 may output light in several wavelengths simultaneously.

In yet another embodiment, instead of producing one final image, eye imaging system 200 may capture and output a plurality of images. For example, in addition to or in lieu of generating the image captured in step 702, CPU 202 may capture one or more images in sequence, with light source 210 emitting light in a different wavelength for each image. In another example, light source 210 may also output light with multiple wavelengths for each image.

Once eye imaging system 200 has sent the final image in step 718 to image analysis system 212, the operation of the algorithm shown in FIG. 7 pertaining to one iteration of an image capture of a final image ends.

It should be noted that although the size and position determination steps described above are described as separate operations, these two steps may also be performed in parallel. In addition, certain aspects of the operations may be combined. For example, the sizes of iris 106 and pupil 104 may be determined from the length of distances d1', d2', d3' and d4' as the iris and pupil are substantially circular in shape. Thus, CPU 202 can determine whether eye 100 is in the proper position of being centered as well as calculate whether the determined size is of the appropriate size to capture the final image.

The embodiments described above are exemplary embodiments of an eye imaging system configured in accordance with the present invention. Those skilled in the art may now make numerous uses of, and departures from, the above-described embodiments without departing from the inventive concepts disclosed herein. Accordingly, the present invention is to be defined solely by the scope of the following claims.

What is claimed is:

1. An apparatus for capturing an image of an eye having an iris comprising a computer-readable medium having computer executable instructions stored thereon, the computer-executable instructions, when executed by a computer, causes the computer to perform a method comprising the steps of:
   determining a plurality of measurement origins in the image;
   detecting an edge of the iris;
   determining a distance from each measurement origin to the edge of the iris; and,
   outputting a final image when each of the determined distances is equal to respective one of a plurality of predetermined lengths.

2. The apparatus of claim 1, wherein the plurality of measurement origins comprises a corner of the image.

3. The apparatus of claim 1, wherein the plurality of measurement origins comprises an edge of the image.

4. The apparatus of claim 1, wherein the step of outputting a final image comprises outputting the captured image.

5. The apparatus of claim 1, wherein the step of outputting a final image occurs when each one of the plurality of predetermined lengths are equal to each other.

6. The apparatus of claim 1, wherein the method further comprising the step of capturing a second final image.

7. The apparatus of claim 6, wherein the final image and the second final image are captured with different parameters.

8. The apparatus of claim 7, wherein the parameter is a resolution.

9. The apparatus of claim 7, wherein the parameter is a size.

10. The apparatus of claim 7, wherein the parameter is a wavelength.

11. The apparatus of claim 1, wherein the method further comprising the step of overlaying an eye feature position marker on a displayed version of the captured image.

12. An apparatus for capturing an image of an eye, the eye having an iris and a pupil, comprising a computer readable medium having computer-executable instructions stored thereon, the computer-executable instructions, when executed by a computer, causes the computer to perform a method comprising the steps of:
    determining a size and location of one of the iris and the pupil;
    comparing the determined size and location to a predetermined size and position; and,
    outputting a final image if the size and location matches the predetermined size and position, respectively.

13. The apparatus of claim 12, wherein the method further comprises the step of capturing the final image.

14. The apparatus of claim 12, wherein the image comprises a plurality of pixels, and the step of determining a size and location of one of the iris and the pupil comprises the step of determining whether each of the plurality of pixels represents one of an iris pixel and a pupil pixel.

15. An apparatus for capturing an image of an eye, the eye including a pupil with a size, comprising a computer readable medium having computer-executable instructions stored thereon, the computer-executable instructions, when executed by a computer, causes the computer to perform a method comprising the steps of:
    manipulating the size of the pupil by exposing the pupil to a light starting at a first intensity level and ending at a second intensity level;
    determine the size of the pupil;
    comparing the determined size to a predetermined size; and
    outputting a final image when the size of the pupil matches the predetermined size.

16. The apparatus of claim 15, wherein the first intensity level is greater than the second intensity.

17. The apparatus of claim 15, wherein the second intensity level is zero.

18. An apparatus for auto-positioning and auto-triggering of a capture of an eye image, comprising a computer readable medium having computer-executable instructions stored thereon, the computer-executable instructions, when executed by a computer, causes the computer to perform a method comprising the steps of:
    capturing a first image of an eye having a pupil, the first image having four corners;
    detecting an edge of the pupil; and,
    determining a distance from each corner of the image to the edge of the pupil along two diagonal paths, each diagonal path defined by two diagonally opposing corners of the first image.

19. The apparatus of claim 18, wherein the method further comprises the step of outputting a final image when the distance from each corner of the image to the edge of the pupil is equal to each other.

20. The apparatus of claim 18, wherein the method further comprises the step of adjusting a size of the pupil by varying the intensity of a visible light source.

21. The apparatus of claim 18, wherein the method further comprises the step of determining the size of the pupil by calculating an average darkness level in the pupil and using this average as a defining threshold for determining the area of the pupil.

* * * * *